United States Patent
Jeon et al.

(10) Patent No.: US 10,004,769 B2
(45) Date of Patent: Jun. 26, 2018

(54) LACTOBACILLUS BREVIS G-101 STRAIN AND USE THEREOF

(71) Applicant: CTC BIO, INC., Seoul (KR)

(72) Inventors: Hong Ryeol Jeon, Suwon-si (KR);
Yoon-Mo Kang, Seoul (KR);
Byeong-Gon Lee, Suwon-si (KR);
Se-Young Kim, Hwaseong-si (KR);
Go-Eun Shin, Incheon (KR)

(73) Assignee: CTC BIO, INC., Seoul (KR)

( * ) Notice: Subject to any disclaimer, the term of this patent is extended or adjusted under 35 U.S.C. 154(b) by 150 days.

(21) Appl. No.: 14/895,886

(22) PCT Filed: Jun. 2, 2014

(86) PCT No.: PCT/KR2014/004901
§ 371 (c)(1),
(2) Date: Dec. 3, 2015

(87) PCT Pub. No.: WO2014/196775
PCT Pub. Date: Dec. 11, 2014

(65) Prior Publication Data
US 2016/0129057 A1    May 12, 2016

(30) Foreign Application Priority Data
Jun. 3, 2013 (KR) .................. 10-2013-0063437

(51) Int. Cl.
*C12N 1/20* (2006.01)
*A61K 35/747* (2015.01)
*C12R 1/24* (2006.01)
*C12P 13/00* (2006.01)

(52) U.S. Cl.
CPC ............. *A61K 35/747* (2013.01); *C12N 1/20* (2013.01); *C12P 13/005* (2013.01); *C12R 1/24* (2013.01); *A23Y 2220/13* (2013.01)

(58) Field of Classification Search
None
See application file for complete search history.

(56) References Cited

U.S. PATENT DOCUMENTS

2010/0173371 A1* 7/2010 Jeon ............. C12N 1/20
435/146

FOREIGN PATENT DOCUMENTS

| KR | 10-2006-0006342 A | 1/2006 |
| KR | 10-2006-0058225 A | 5/2006 |
| KR | 10-2009-0116051 | 11/2009 |
| KR | 10-2012-0007917 | 1/2012 |
| WO | 2012-086909 A2 | 6/2012 |

OTHER PUBLICATIONS

Jang et al., J. Appl. Microbiol., vol. 115, Issue 3, Sep. 2013, pp. 888-896.*
Choi et al., J. Microbiol. Biotechnol. (2006), vol. 16(4), 562-568.*
Ronka et al., International Journal of Food Microbiology 83 (2003) 63-74.*
Jang S. E. et al., "*Lactobacillus brevis* G-101 ameliorates colitis in mice by inhibiting NF-kB, MAPK and AKT pathways and by polarizing M1 macrophages to M2-like macrophages", Journal of Applied Microbiology, Epub, Jul. 1, 2013, vol. 115, No. 3, pp. 888-896.
International Search Report dated Oct. 22, 2014 of PCT/KR2014/004901 which is the parent application and its English translation—6 pages.
Sang-Hee Lee, "Production of Y-Aminobutyric Acid by *Lactobacillus brevis* GD-16 Isolaed from Kimchi", Dec. 2010.

* cited by examiner

*Primary Examiner* — Irene Marx
(74) *Attorney, Agent, or Firm* — Knobbe Martens Olson & Bear LLP

(57) ABSTRACT

The present invention relates to a novel *Lactobacillus brevis* G-101 strain capable of decomposing monosodium L-glutamate (MSG), and a functional health food, a pharmaceutical composition, or a food product comprising the same as an active ingredient. More specifically, the strain is effective in reducing in vivo blood MSG levels of animals and attenuating MSG Symptom Complex, and thus can be used in a functional health food, a pharmaceutical composition, or a food product aiming to prevent in vivo absorption of MSG, which is known to be harmful, and improve the MSG Symptom Complex.

2 Claims, 15 Drawing Sheets

LACTOBACILLUS BREVIS G-101 STRAIN AND USE THEREOF

TECHNICAL FIELD

The present disclosure relates to a novel *Lactobacillus* strain capable of decomposing monosodium L-glutamate, a composition comprising the same as an active ingredient, and a use thereof.

The present application claims the priority of Korean Patent Application No. 10-2013-0063437 filed on Jun. 3, 2013 with the Korean Intellectual Property Office, all contents disclosed in the specification and drawings of which is incorporated herein by reference in its entirety.

BACKGROUND ART

*Lactobacillus* is one of the major bacteria present in an intestinal tract of animals including human. Due to advantageous effects on in vivo physiological activity of an animal, the *Lactobacillus* has been variously added to diverse probiotic products.

Meanwhile, monosodium L-glutamate (MSG) that is used to food additives and chemical seasonings for taste and flavor has been used worldwide since it was found from kelp extract by Dr. Ikeda in 1907 and developed as a product by Ajinomoto Co., Japan.

Natural foods containing relatively large amount of glutamic acid, which is a major material of the MSG are breast milk, weed, kelp, mushroom, meats, tomato, parmesan cheese, beans and the like, and when it is taken in the form of natural food, there is no example reported side effects or pathological symptoms.

However, after Chinese-American physician Kwok confirmed that some people taken excessive MSG showed various symptoms such as headache, weakness, rigidity and chest pain in 1968, controversy over harmful effect of the MSG was started for the first time. Then, in 1981, the New England Journal of Medicine reported that two asthma patients experienced asthma attack 12 hours after eating at Chinese restaurant (Baker G J et al. 1981), and reported that intake of excessive amount of MSG causes brain cell damage and endocrine system disruption, and in particular, it is harmful to infants, and also it causes eyes and brain damages after infant mice take commercially available MSG-added infant food (Olney J W, Sharpe L G 1969). Further, it was confirmed that after orally administrating 0.5 g/Kg body weight of MSG into young mice (10~12 days-old), 52% of the tested mice showed neuronal cell damage at a rate of 100% every 1 g administration (Lowe C U et al. 1970). The term 'MSG Symptom Complex (MSC)' was started being used in that the MSG is not a problem of only Chinese restaurant. Also, when taking 2.5 g or more of MSG, symptoms such as headache, muscle stress, muscle numbness, weakness, facial flushing and the like was shown in the double blind, placebo controlled study (placebo, 1.25, 2.5, 5 g MSG) of Yang W H et al. (1997), and the symptom study after taking MSG of Schaumburg et al. (1969) reported that symptoms of the MSG Symptom Complex are insensibility or numbness, headache, migraine, palpitation, chest tightness, weakness, aching, facial flushing, cold sweating, lacrimation, syncope, dizziness, shudder attacks, paresthesias, arrhythmias, tachycardia. Besides that, it was reported that excess MSG intake causes or aggravates asthma, atopic dermatitis, respiratory arrhythmia, nervous disease, indigestion and the like (Allen D H et al, 1987), Federation of American Societies in Experimental Biology (FASWB) reported through a report in 1995 that some sensitive people may show allergy reaction as the MSG Symptom Complex, and in some serious intractable asthma patients, asthma may worsen after taking the MSG in an amount of about 0.5 to 2.5 g per day (Geha et al. 2000).

However, despite these harmful effects of the MSG, the MSG is used as a taste enhancer for cooking at home and restaurant, and as an additive for food processing production; and it is known that in advanced countries, average daily intake of MSG per person is 0.3 to 1.0 g (Geha R S et al. 2000), and in Korea, the MSG intake is the highest as 1.977 g among the currently known countries (Jeong, Youngsub, Asiatoday, 2013). It is expected that it may be difficult to reduce MSG consumption in the future due to eating out culture and growing trend of instant food consumption of busy modern people.

DISCLOSURE

Technical Problem

The present disclosure is designed to solve the problems of the related art, and therefore the present disclosure is directed to providing a *Lactobacillus brevis* G-101 strain capable of decomposing monosodium L-glutamate, and a composition comprising the strain as an active ingredient, and a use thereof, thereby inhibiting in vivo absorption of harmful MSG and treating, preventing or improving MSG Symptom Complex.

Other objects and advantages of the present disclosure will be understood by the following description, and it is understood that these can be achieved by means, methods or a combination thereof which are defined in the claims.

Technical Solution

In order to solve the above problems, the present invention provides a *Lactobacillus brevis* G-101 strain and a use of the strain.

More particularly, first, it relates to a method for inhibiting in vivo MSG absorption of an animal by using probiotic activity of the *Lactobacillus brevis* G-101 strain, a composition for inhibiting in vivo MSG absorption of an animal, which comprises the *Lactobacillus brevis* G-101 strain as an active ingredient, and a use of the *Lactobacillus brevis* G-101 strain for inhibiting in vivo MSG absorption of an animal.

Second, it relates to a method for decomposing MSG by using the *Lactobacillus brevis* G-101 strain, a method for converting MSG into γ-aminobutyric acid, which comprises contacting the *Lactobacillus brevis* G-101 strain with a sample containing MSG followed by culturing thereof, a method for producing GABA from MSG, which comprises contacting the *Lactobacillus brevis* G-101 strain with a sample containing MSG followed by culturing thereof, a composition for decomposing MSG, which comprises the *Lactobacillus brevis* G-101 strain as an active ingredient, a composition for converting MSG into GABA, which comprises the *Lactobacillus brevis* G-101 strain as an active ingredient, a composition for producing GABA from MSG, which comprises the *Lactobacillus brevis* G-101 strain as an active ingredient, a use of the *Lactobacillus brevis* G-101 strain for decomposing MSG, a use of the *Lactobacillus brevis* G-101 strain for converting MSG into GABA, and a use of the *Lactobacillus brevis* G-101 strain for producing GABA from MSG.

Third, a method for enhancing anti-inflammatory ability of a subject, which comprises administrating the *Lactobacillus brevis* G-101 strain into the subject who needs anti-inflammatory activity enhancing effect of the *Lactobacillus brevis* G-101 strain, by using the effect of the strain, a method for preventing, improving or treating inflammatory diseases, a composition for preventing, improving or treating inflammatory disease, which comprises the *Lactobacillus brevis* G-101 strain as an active ingredient, a composition for enhancing anti-inflammatory ability of a subject, a use of the *Lactobacillus brevis* G-101 strain for enhancing anti-inflammatory ability of a subject, and a use of the *Lactobacillus brevis* G-101 strain for preventing, improving or treating inflammatory diseases.

Fourth, a method for preventing, improving or treating MSG Symptom Complex of a subject, which comprises administrating the *Lactobacillus brevis* G-101 strain into the subject by using MSG Symptom Complex attenuation effect of the *Lactobacillus brevis* G-101 strain, a composition for preventing, improving or treating MSG Symptom Complex, which comprises the *Lactobacillus brevis* G-101 strain as an active ingredient, and a use of the *Lactobacillus brevis* G-101 strain for preventing, improving or treating MSG Symptom Complex of a subject.

Hereinafter, the present invention will be described.

In one aspect, the present invention provides a *Lactobacillus brevis* G-101 strain (Accession Number: KCCM11412P).

Herein, the term, "strain" includes live bacteria (probiotic), killed bacteria, dried bacteria or strain culture solution. Further, the term, "culture solution" includes culture solution itself, in which the strain is cultured in a suitable medium, filtrate (filtered solution or centrifuged supernatant), which is obtained by filtering or centrifuging the culture solution to remove the strain, concentrated solution, which is obtained by concentrating the filtrate, cell lysate, which is obtained by sonicating the culture solution or treating the culture solution with lysozyme, and the like. The medium used for manufacturing the culture solution is not limited to a specific type, and it may be, for example, any medium containing general medium for culturing microorganism without limitation. Further, the culture solution can further contain any additive depending on the specific purpose. For example, in order to maximize the effect of the culture according to the present invention on inhibiting in vivo MSG absorption of an animal, any conventional MSG absorption inhibitor, which is known to a person skilled in the art, may be contained in a suitable amount, and at this time, it is obvious that specific content and concentration rage of the active ingredient can be easily determined by a person skilled in the art through repetitive experiments and the like.

The present inventors tried to isolate *Lactobacillus* strains having an effect of inhibiting in vivo MSG absorption of an animal, and as a result, they isolated a strain having excellent MSG decomposing ability from kimchi, *Lactobacillus brevis* G-101 strain, and confirmed that the strain has probiotic activity based on its viability in digestive canal, in particular, the effect of inhibiting in vivo MSG absorption of an animal. More specifically, the present inventors confirmed that as a result of administrating MSG after administration of the *Lactobacillus brevis* G-101 strain and then measuring MSG concentration in digestive canal and blood, MSG concentration, which is absorbed from the digestive canal into blood, is reduced by the administration of the *Lactobacillus brevis* G-101 strain, and blood MSG concentration is inversely proportional to the number of the administered *Lactobacillus brevis* G-101 strain. Accordingly, the strain was deposited to Korean Culture Center of Microorganisms (KCCM) on Apr. 30, 2013 under the Accession Number KCCM11412P.

In addition, the present inventors confirmed that as a result of culturing the *Lactobacillus brevis* G-101 strain (Accession Number: KCCM11412P) with MSG, the *Lactobacillus brevis* G-101 strain (Accession Number: KCCM11412P) has an effect of converting MSG into GABA.

Further, additionally, the present inventors confirmed that the *Lactobacillus brevis* G-101 strain (Accession Number: KCCM11412P) has effects of increasing anti-inflammatory cytokine production, inhibiting inflammatory cytokine production, controlling the upper pathway of the inflammatory reaction pathway, and controlling macrophage polarization, and also it has an effect of inhibiting inflammatory diseases, in particular, anti-colitis effect.

Further, additionally, the present inventors confirmed that as a result of a clinical test subjected to the *Lactobacillus brevis* G-101 strain (Accession Number: KCCM11412P), the strain has MSG Symptom Complex attenuation effect.

The *Lactobacillus brevis* G-101 (Accession Number: KCCM11412P) has various useful effects as described above, and therefore, it can be used as for various uses.

Thus, the present invention provides a composition comprising the *Lactobacillus brevis* G-101 (Accession Number: KCCM11412P) as an active ingredient.

The composition may be used in various forms such as probiotics, functional health foods, foods, food supplement additives, pharmaceutical compositions, cosmetic compositions, feed compositions (feeds or feed additives and the like) or quasi-drugs and the like.

The composition has effects of inhibiting in vivo MSG absorption of an animal, converting MSG into GABA, anti-inflammatory activity and MSG Symptom Complex attenuation. Thus, it can be used as, for example, a composition for inhibiting in vivo MSG absorption of an animal, a composition for converting MSG into GAB A, a composition for producing GABA from MSG, a composition for enhancing anti-inflammatory activity, a composition for preventing, improving or treating inflammatory diseases, or a composition for preventing, improving or treating MSG Symptom Complex.

Further, the present invention provides a method for inhibiting in vivo MSG absorption of an animal by using the strain or the composition, a method for converting MSG into GABA, a method for producing GABA from MSG, a method for enhancing anti-inflammatory activity, a method for preventing, improving or treating inflammatory diseases, or a method for preventing, improving or treating MSG Symptom Complex.

Further, the present invention provides a use of the *Lactobacillus brevis* G-101 for decomposing in vivo MSG in an animal, a use of the *Lactobacillus brevis* G-101 for converting MSG into γ-aminobutyric acid, a use of the *Lactobacillus brevis* G-101 for producing GABA from MSG, a use of the *Lactobacillus brevis* G-101 for manufacturing a pharmaceutical preparation for preventing, improving or treating inflammatory diseases, or a use of the *Lactobacillus brevis* G-101 for manufacturing a pharmaceutical preparation for preventing, improving or treating MSG Symptom Complex.

Herein, the term 'inhibiting in vivo MSG absorption' means all acts, which stop, alleviate or delay the absorption of MSG into blood by administration of the *Lactobacillus brevis* G-101 according to the present invention (Accession Number: KCCM11412P).

Herein, the term 'converting (or producing) MSG into GABA' means that a part or all of MSG is decomposed and changed to GABA by contacting the *Lactobacillus brevis* G-101 according to the present invention (Accession Number: KCCM11412P) with a MSG-containing sample. The MSG-containing sample may be contained together with the *Lactobacillus brevis* G-101 (Accession Number: KCCM11412P) in a composition comprising the strain.

The 'γ-aminobutyric acid' is an amino acid having the carbon number of 4, which constitutes non-protein, and it plays a role of neurotransmitter in brain and also has various physiological functions such as brain function acceleration, mental stability, blood pressure lowering, diuresis, liver function enhancement, obesity prevention, alcohol metabolism acceleration, deodorization and the like. In particular, it was registered as a drug, and used for treating headache, ringing in ears, decline in desire and the like caused by stroke or cerebral artery aftereffect. It is broadly distributed in diverse vegetables, fruits, rice, beans and the like, but it is not suitable for showing physiological functions because its content in natural foods is too low.

Herein, the term 'preventing' means all acts, which inhibit or delay progression of inflammatory diseases by administrating the strain according to the present invention or a composition comprising the strain as an active ingredient.

Herein, the term 'treating' or 'improving' means all acts, which change a turn of symptoms of inflammatory diseases for the better or change the symptoms favorably by administrating the strain according to the present invention or a composition comprising the strain as an active ingredient.

The term 'administrating' means providing a certain strain according to the present invention or a certain composition comprising the stain as an active ingredient to a subject by any suitable method.

The 'subject' means an animal, which is expected to exert effects by the *Lactobacillus brevis* G-101 (Accession Number: KCCM11412P) by administrating the strain according to the present invention or a composition comprising the strain as an active ingredient, and the animal includes, for example, dog, monkey, goat, pig, mouse and the like, and preferably human.

The 'anti-inflammatory activity' refers to an ability, which can inhibit operation of an inflammatory system in the body, and includes, for example, enhancing expression of anti-inflammatory cytokines or inhibiting expression of inflammatory cytokines.

The 'inflammatory disease' means all diseases having inflammation as a major lesion, preferably, it means inflammatory bowel disease; and the inflammatory bowel disease means chronic inflammation occurring in the bowels, and it includes, for example, ulcerative colitis (UC) or crohn's disease (CD).

Herein, the term 'MSG Symptom Complex' means side effects or abnormal symptom caused by MSG intake including: headache, muscle stress, muscle numbness, weakness, facial flushing, insensibility or numbness, migraine, palpitation, chest tightness, lethargy, aching, cold sweating, lacrimation, syncope, dizziness, shudder attacks, paresthesias, arrhythmias, tachycardia, asthma, atopic dermatitis, respiratory arrhythmia, nervous disease, indigestion, thirstiness, drowsiness, nausea, vomiting, allergy reaction, asthma attack, brain cell damage or endocrine system disturbance and the like.

Herein, the term 'MSG Symptom Complex attenuation' means all effects, which stop, alleviate or delay MSG Symptom Complex in a subject by administrating the strain according to the present invention or a composition comprising the strain as an active ingredient.

Herein, the term 'preventing' means all acts, which inhibit or delay progression of MSG Symptom Complex by administrating the strain according to the present invention or a composition comprising the strain as an active ingredient.

Herein, the term 'treating' or 'improving' means all acts, which take a turn of MSG Symptom Complex for the better, or alleviate, stop or favorably change MSG Symptom Complex by administrating the strain according to the present invention or a composition comprising the strain as an active ingredient.

The 'administrating' means providing a certain strain according to the present invention or a certain composition comprising the stain as an active ingredient to a subject by any suitable method.

The 'subject' means an animal, which is expected to exert effects by the *Lactobacillus brevis* G-101 (Accession Number: KCCM11412P) by administrating the strain according to the present invention or a composition comprising the strain as an active ingredient, and the animal includes, for example, dog, monkey, goat, pig, mouse and the like, and preferably human.

In one aspect, the present invention provides a functional health food comprising the *Lactobacillus brevis* G-101 (Accession Number: KCCM11412P) as an active ingredient.

More specifically, the present invention provides a functional health food for inhibiting in vivo MSG absorption of an animal, which comprises the *Lactobacillus brevis* G-101 (Accession Number: KCCM11412P) as an active ingredient. The present invention provides a functional health food for preventing or improving inflammatory diseases, which comprises the *Lactobacillus brevis* G-101 (Accession Number: KCCM11412P) as an active ingredient. Further, the present invention provides a functional health food for preventing or improving MSG Symptom Complex, which comprises the *Lactobacillus brevis* G-101 (Accession Number: KCCM11412P) as an active ingredient.

Herein, the term 'functional health food' refers to a food, which uses a specific ingredient as a raw material or is manufactured and processed by methods such as extracting, concentrating, purifying and mixing a specific ingredient contained in the raw material of the food for the purpose of health supplement, and also it refers to a food, which is designed and processed to sufficiently exert body modulating functions such as host defense, biorhythm control, prevention or recovery of disease and the like against a living body by the ingredient, thereby conducting functions related to disease prevention or health recovery and the like.

When using the *Lactobacillus brevis* G-101 according to the present invention (Accession Number: KCCM11412P) as a functional health food, it can be added as it is or used together with other food or food ingredients, and it can be selected as needed and properly used. Further, the amount of the *Lactobacillus brevis* G-101 (Accession Number: KCCM11412P) to be mixed may be suitably determined depending on its purpose of use. The *Lactobacillus brevis* G-101 according to the present invention (Accession Number: KCCM11412P) has guaranteed biostability, and shows activity increasing effect in proportion to concentration. Thus, it is obvious that it can be used in a proper amount without limitation to a specific range.

Further, a kind of the functional health food, in which the *Lactobacillus brevis* G-101 according to the present invention (Accession Number: KCCM11412P) may be used, is not particularly limited. For example, it may be ramen, other noodles, beverages, teas, drinks, alcoholic beverages, all sorts of soups, meats, sausages, breads, chocolates, candies, snacks, pizza, gums, dairy products including ice creams, or vitamin complex and the like. In particular, because the *Lactobacillus brevis* G-101 according to the present invention (Accession Number: KCCM11412P) has excellent viability in digestive canal and excellent effect of inhibiting in vivo MSG absorption, it is particularly suitable to produce various *Lactobacillus* fermented milk or fermented product. The fermented milk functional health food may be, for example, yogurt, Calpis, cheese, butter and the like, and the fermented product may be tofu, fermented soybean paste (toenjang), fast-fermented soybean paste (cheonggukjang), jelly, kimchi and the like. The fermented milk or the fermented product may be easily manufactured by only replacing a strain with the *Lactobacillus brevis* G-101 according to the present invention (Accession Number: KCCM11412P) in a common manufacturing method.

Further, the *Lactobacillus brevis* G-101 according to the present invention (Accession Number: KCCM11412P) may be mixed with other suitable auxiliary ingredients and known additives, which can be commonly contained in the functional health food according to selection of a person skilled in the art. The known additive may include other microorganism, which can be used with the strain according to the present invention.

Further, in other aspect, the present invention provides a food comprising the *Lactobacillus brevis* G-101 (Accession Number: KCCM11412P) as an active ingredient.

More specifically, the present invention provides a food for inhibiting in vivo MSG absorption of an animal, which comprises the *Lactobacillus brevis* G-101 (Accession Number: KCCM11412P) as an active ingredient. The present invention provides a food for preventing or improving inflammatory diseases, which comprises the *Lactobacillus brevis* G-101 (Accession Number: KCCM11412P) as an active ingredient. Further, the present invention provides a food for preventing or improving MSG Symptom Complex, which comprises the *Lactobacillus brevis* G-101 (Accession Number: KCCM11412P) as an active ingredient.

When using the *Lactobacillus brevis* G-101 according to the present invention (Accession Number: KCCM11412P) as a food, it can be added as it is or used together with other food or food ingredients, and it can be selected as needed and properly used.

Further, the amount of the *Lactobacillus brevis* G-101 (Accession Number: KCCM11412P) to be mixed may be suitably determined according to its purpose of use. The *Lactobacillus brevis* G-101 according to the present invention (Accession Number: KCCM11412P) has guaranteed biostability, and shows activity increasing effect in proportion to concentration. Thus, it is obvious that it can be used in a proper amount without limitation to a specific range.

Further, a kind of the functional health food, in which the *Lactobacillus brevis* G-101 according to the present invention (Accession Number: KCCM11412P) may be used, is not particularly limited. For example, it may be ramen, other noodles, beverages, teas, drinks, alcoholic beverages, all sorts of soups, meats, sausages, breads, chocolates, candies, snacks, pizza, gums, dairy products including ice creams, or vitamin complex and the like. In particular, because the *Lactobacillus brevis* G-101 according to the present invention (Accession Number: KCCM11412P) has excellent viability in digestive canal and excellent effect of inhibiting in vivo MSG absorption, it is particularly suitable to produce various *Lactobacillus* fermented milk or fermented product. The fermented milk food may be, for example, yogurt, Calpis, cheese, butter and the like, and the fermented product may be tofu, fermented soybean paste (toenjang), fast-fermented soybean paste (cheonggukjang), jelly, kimchi and the like. The fermented milk or the fermented product may be easily manufactured by only replacing a strain with the *Lactobacillus brevis* G-101 according to the present invention (Accession Number: KCCM11412P) in a common manufacturing method.

Further, the *Lactobacillus brevis* G-101 according to the present invention (Accession Number: KCCM11412P) may be mixed with other suitable auxiliary ingredients and known additives, which can be commonly contained in the food according to selection of a person skilled in the art.

Further, in other aspect, the present invention provides a pharmaceutical composition comprising the *Lactobacillus brevis* G-101 (Accession Number: KCCM11412P) as an active ingredient.

More specifically, the present invention provides a pharmaceutical composition for inhibiting in vivo MSG absorption of an animal, which comprises the *Lactobacillus brevis* G-101 (Accession Number: KCCM11412P) as an active ingredient. The present invention provides a pharmaceutical composition for preventing or treating inflammatory diseases, which comprises the *Lactobacillus brevis* G-101 (Accession Number: KCCM11412P) as an active ingredient. Further, the present invention provides a pharmaceutical composition for preventing or improving MSG Symptom Complex, which comprises the *Lactobacillus brevis* G-101 (Accession Number: KCCM11412P) as an active ingredient.

The pharmaceutical composition comprising the *Lactobacillus brevis* G-101 according to the present invention (Accession Number: KCCM11412P) as an active ingredient may be directly used as a composition itself having an effect of inhibiting in vivo MSG absorption of an animal, an effect of converting MSG into GABA, an effect of improving, preventing or treating inflammatory diseases, or an effect of preventing, improving or treating MSG Symptom Complex, and also may be used as an auxiliary substance.

The pharmaceutical composition according to the present invention may include only the *Lactobacillus brevis* G-101 (Accession Number: KCCM11412P) in a pharmaceutically effective amount or may include at least one pharmaceutically acceptable carrier, excipient or diluent. In the above, the 'pharmaceutically effective amount' refers to an enough amount to exert the effect of inhibiting in vivo MSG absorption of an animal, the effect of converting MSG into GABA, or the effect of preventing or treating inflammatory diseases. The 'pharmaceutically acceptable' refers to a composition, which is physiologically acceptable, and commonly causes no allergy reaction such as gastroenteric disorder and dizziness or other similar reaction when it is administered into human.

The pharmaceutical composition according to the present invention may be administered through various routes, including oral, transdermal, subcutaneous, intravenous or intramuscular routes as needed, and it may be provided in the form of a general medicinal preparation.

The pharmaceutical composition according to the present invention may be formulated into various formulations, and in this case, it may be prepared by using commonly used diluent or excipient such as filler, weighting agent, binder, wetting agent, disintegrant, surfactant and the like. A solid formulation for oral administration includes tablet, pill, powder, granule, capsule and the like, and this solid formulation may be prepared by mixing the *Lactobacillus brevis*

G-101 (Accession Number: KCCM11412P) with at least one excipient such as calcium carbonate, sucrose, lactose, gelatin and the like. Further, besides the simple excipient, lubricant such as magnesium stearate, talc and the like is also used. Liquid formulation for oral administration may include suspension, oral liquid, emulsion, syrup and the like, and commonly used simple diluent such as water, liquid paraffin and diverse excipient such as wetting agent, sweetening agent, flavoring agent, preservative and the like may be included.

The content of the *Lactobacillus brevis* G-101 (Accession Number: KCCM11412P) in the pharmaceutical composition according to the present invention may be properly selected according to degree of absorption or excretion rate of the active ingredient in the body, and age, gender and condition of a subject, and the like.

The pharmaceutical composition according to the present invention may be used independently, and also it may be used as a combination with proper other treatment methods (for example, methods using surgery, radiation therapy, hormone therapy, chemotherapy and biologic response modifier and the like), which commonly has anti-inflammatory activity enhancing effect, according to selection of a person skilled in the art.

Advantageous Effects

The *Lactobacillus brevis* G-101 according to the present invention is effective to improve, prevent and treat inflammatory diseases due to its anti-inflammatory activity, has excellent MSG decomposing ability, in particular, exerts superior effect to inhibit in vivo MSG absorption of an animal based on probiotic activity, which can maintain the activity of the strain in digestive canal, and exerts excellent MSG Symptom Complex attenuation effect. Thus, it is expected to be used as various types of uses, for example, a functional health food, a pharmaceutical composition, and a food.

DESCRIPTION OF DRAWINGS

The accompanying drawings illustrate embodiments of the present disclosure and, together with the foregoing disclosure, serve to provide further understanding of the technical features of the present disclosure. However, the present disclosure is not to be construed as being limited to the drawings.

(Con: control group, MSG: group treated with only MSG, G101L: group treated with *Lactobacillus brevis* $1 \times 10^9$ CFU/rat, G101H: group treated with *Lactobacillus brevis* $1 \times 10^{10}$ CFU/rat)

Figure 2:
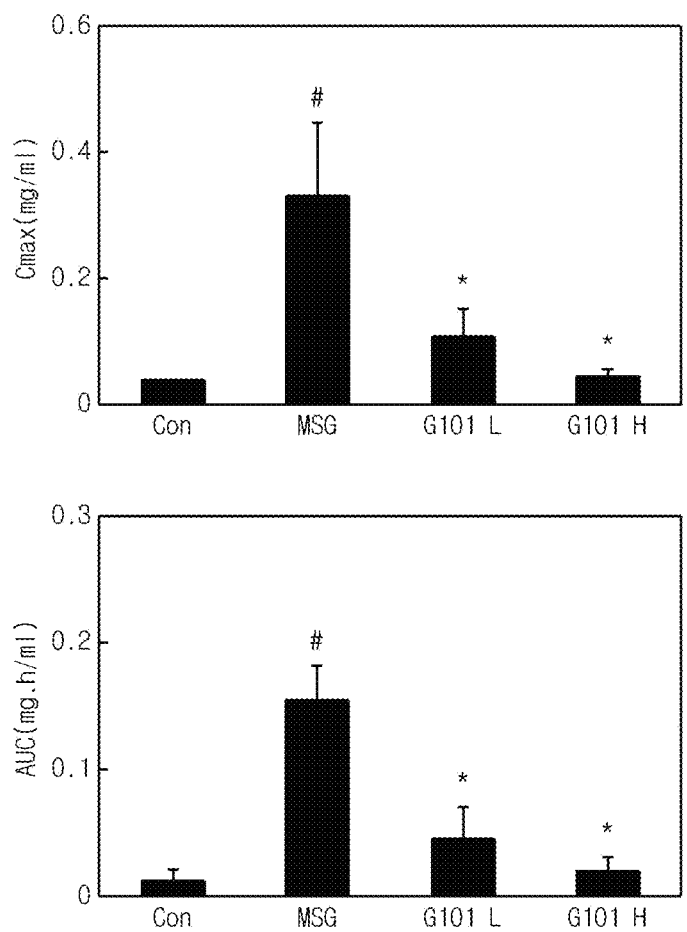

FIG. 2 shows blood MSG Cmax value (left) and AUC value (right) after administering MSG into the rats administered with the *Lactobacillus brevis* G-101.

(Con: control group, MSG: group treated with only MSG, G101L: group treated with *Lactobacillus brevis* $1 \times 10^9$ CFU/rat, G101H: group treated with *Lactobacillus brevis* $1 \times 10^{10}$ CFU/rat)

Figure 3A:
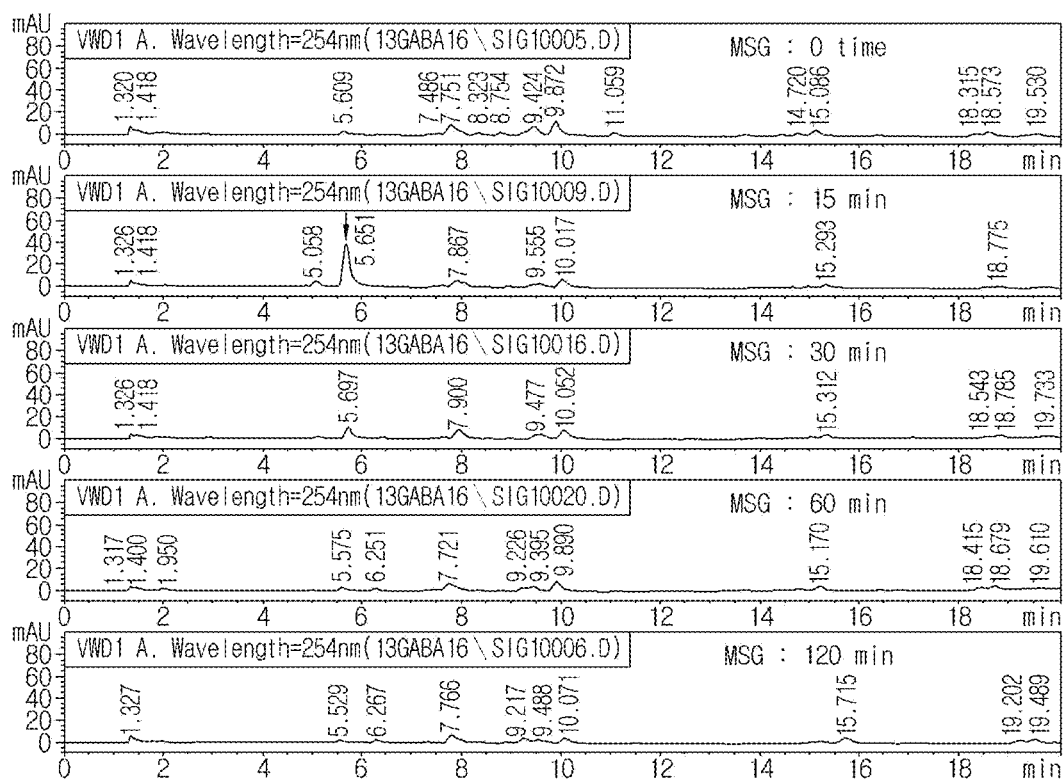
Figure 3B:
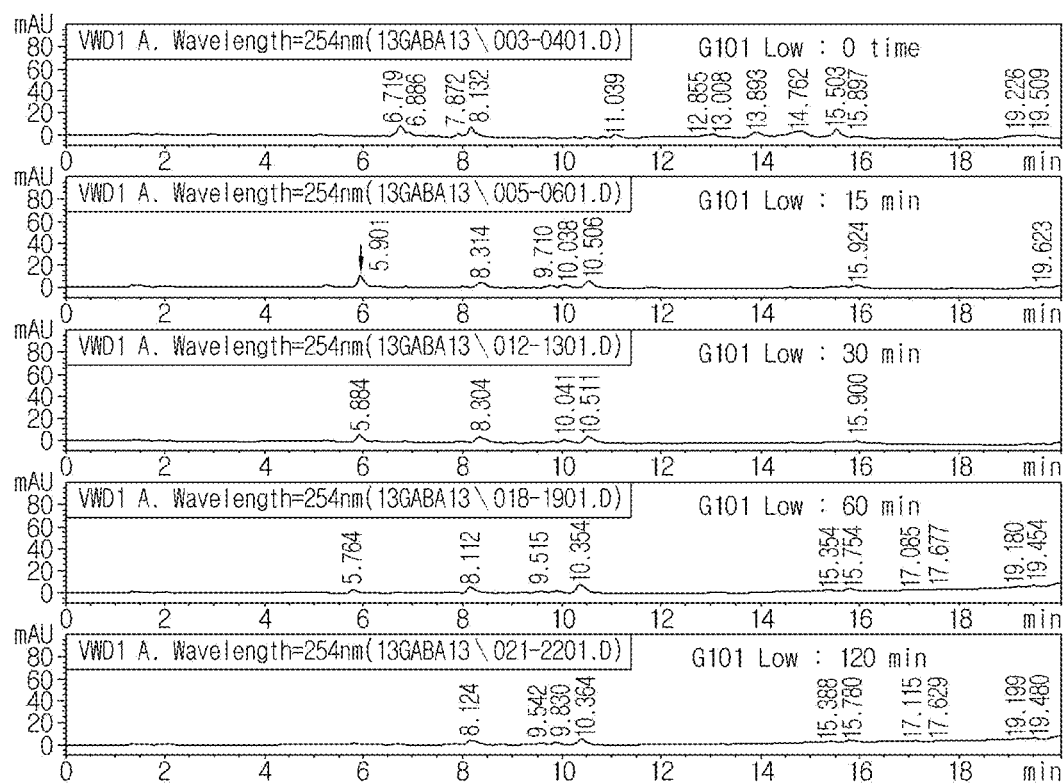
Figure 3C:
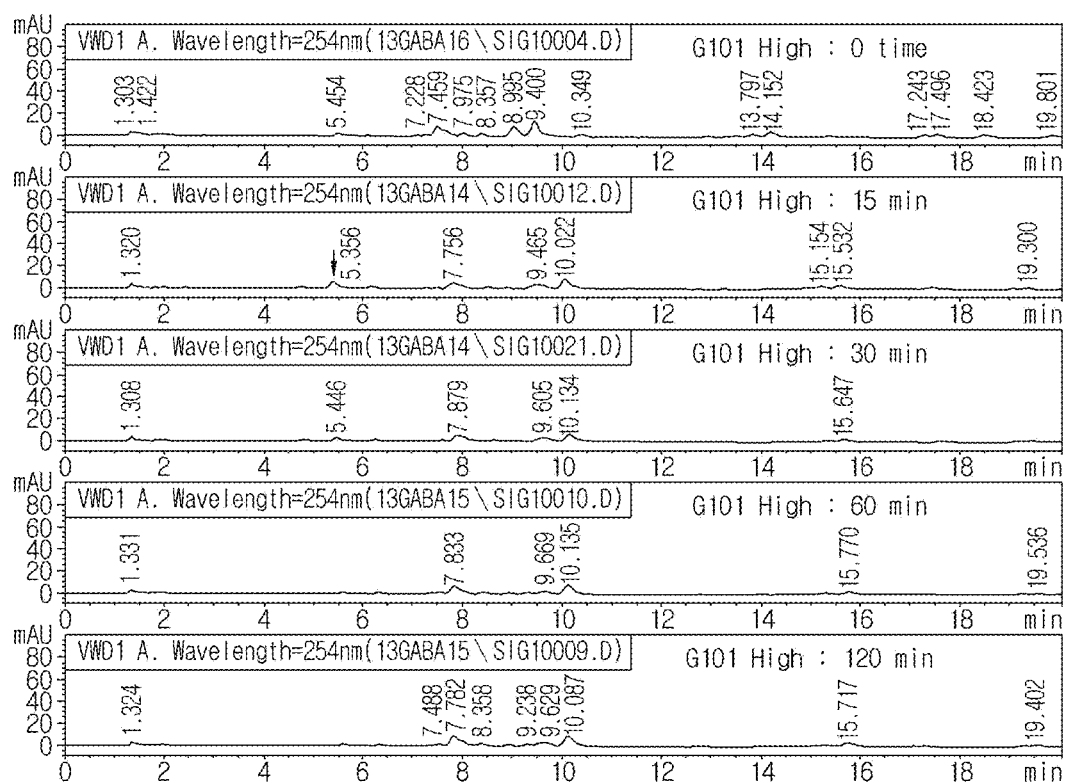

FIG. 3a to FIG. 3c show HPLC Chromatogram showing blood MSG concentration over time after administering MSG into the rats administered with the *Lactobacillus brevis* G-101. FIG. 3a is the result of HPLC Chromatogram subjected to the group treated with only MSG (group not treated with *Lactobacillus brevis* G-101), FIG. 3b is the result of HPLC Chromatogram subjected to the group treated with *Lactobacillus brevis* G-101 $1 \times 10^9$ CFU/rat, and FIG. 3c is the result of the HPLC Chromatogram subjected to the group treated with *Lactobacillus brevis* G-101 $1 \times 10^{10}$ CFU/rat.

(Con: control group, MSG: group treated with only MSG, G101 Low: group treated with *Lactobacillus brevis* $1 \times 10^9$ CFU/rat, G101 High: group treated with *Lactobacillus brevis* $1 \times 10^{10}$ CFU/rat, Arrow: MSG)

Figure 4A:
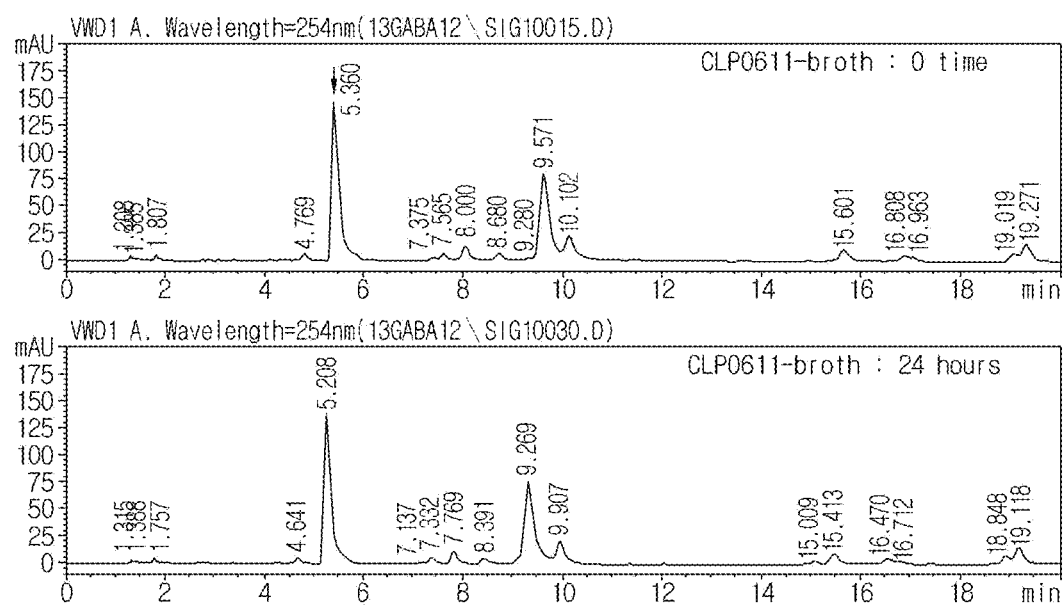
Figure 4B:
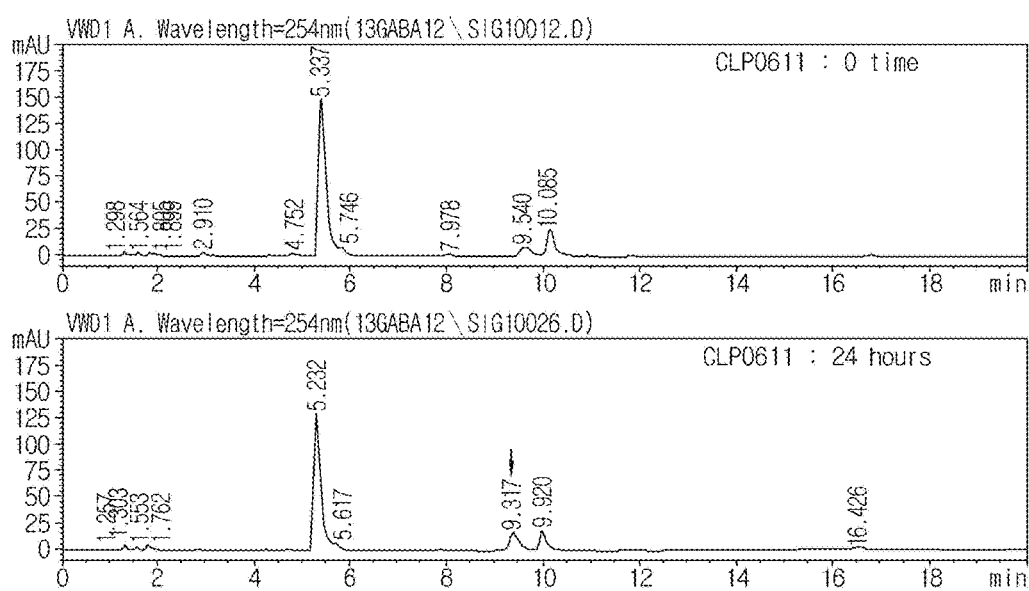

FIG. 4a and FIG. 4b show HPLC Chromatograms of reaction mixtures incubated with MSG in the presence of *Lactobacillus plantarum* CLP-0611. FIG. 4a is the result of the HPLC Chromatogram subjected to the group culturing the *Lactobacillus plantarum* CLP-0611 in MSG-added MRS broth, and FIG. 4b is the result of HPLC Chromatogram subjected to the group in which the *Lactobacillus plantarum* CLP-0611 cultured in MRS broth was centrifuged to collect only its cell, and the cell was added into MSG-added sterilized purified water and then reacted. (thick arrow: MSG, thin arrow: GABA)

Figure 5A:
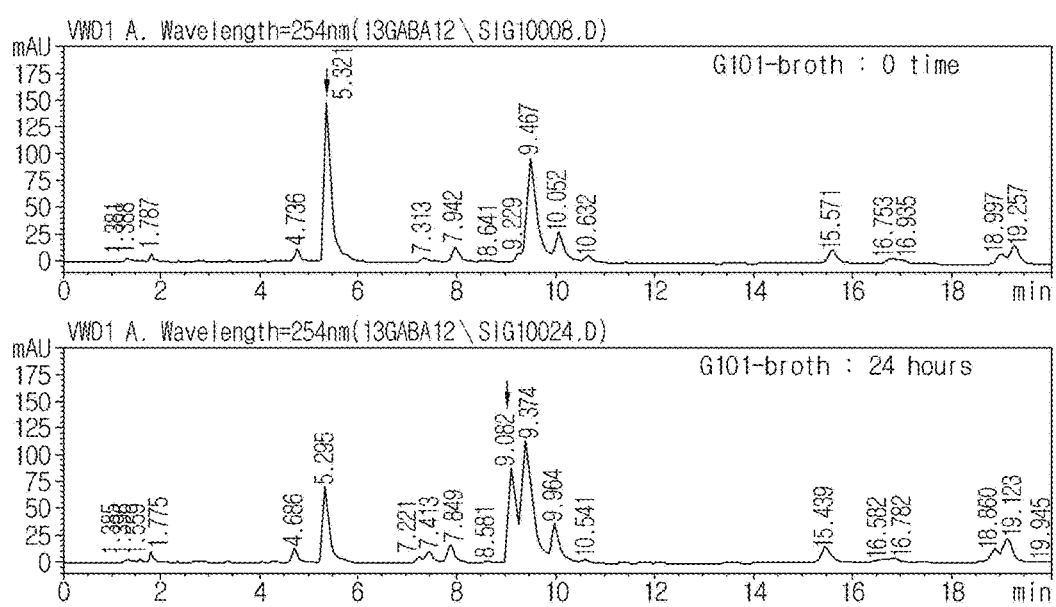
Figure 5B:
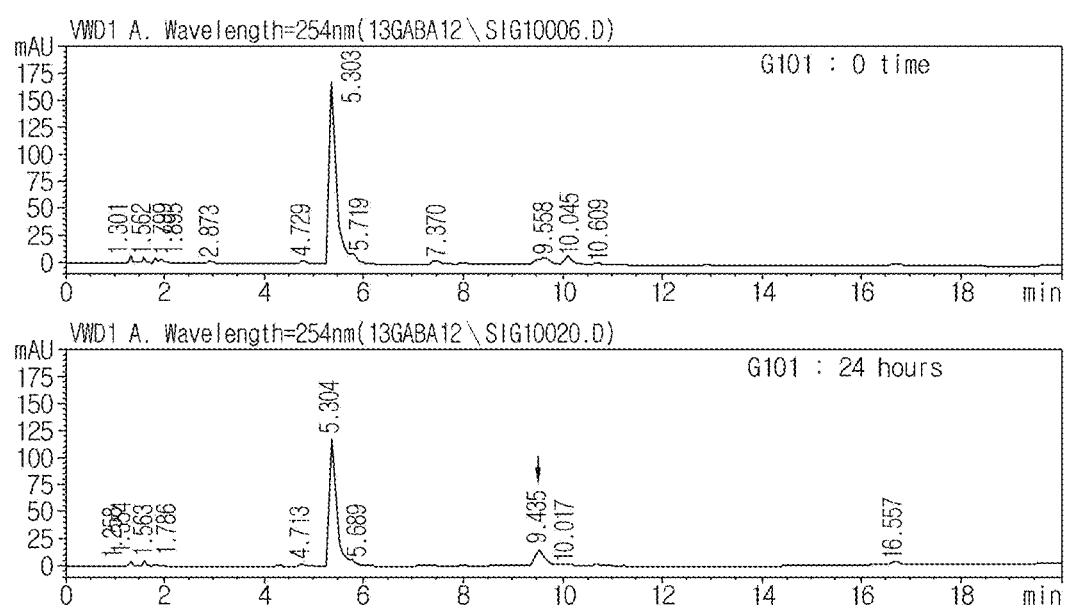

FIG. 5a and FIG. 5b show HPLC Chromatogram of reaction mixtures incubated with MSG in the presence of *Lactobacillus brevis* G-101. FIG. 5a is the result of the HPLC Chromatogram subjected to the group culturing the *Lactobacillus brevis* G-101 in MSG-added MRS broth, and FIG. 5b is the result of HPLC Chromatogram subjected to the group in which the *Lactobacillus brevis* G-101 cultured in MRS broth was centrifuged to collect only its cell, and the cell was added into MSG-added sterilized purified water and then reacted. (thick arrow: MSG, thin arrow: GABA)

Figure 6A:
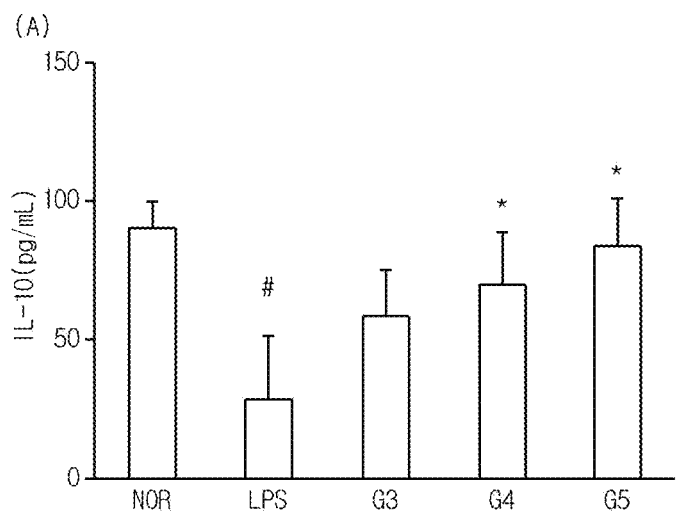
Figure 6B:
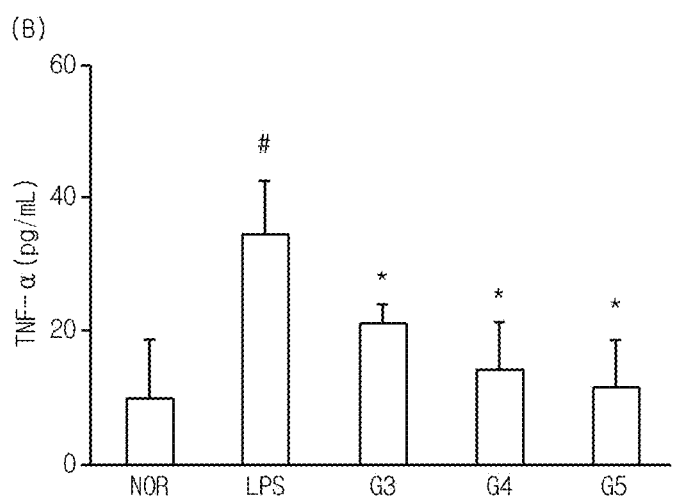
Figure 6C:
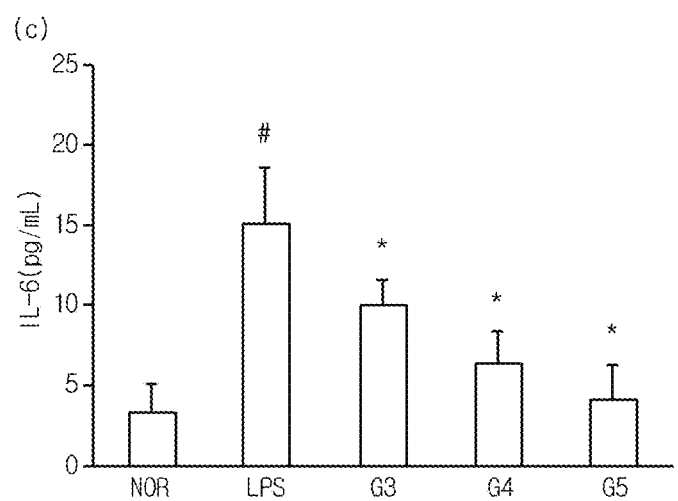
Figure 6D:
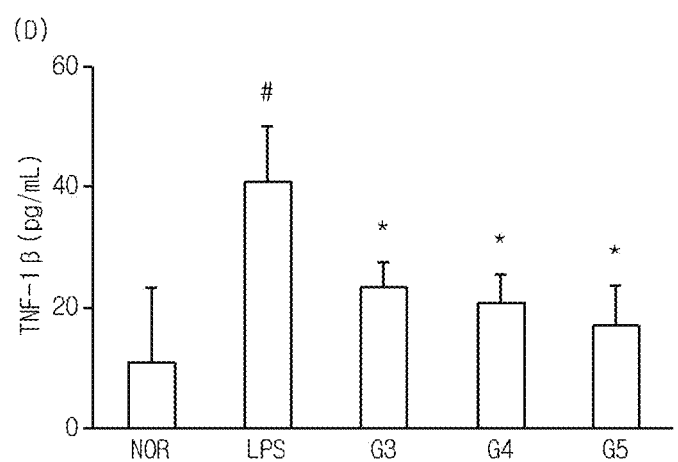

FIG. 6a to FIG. 6d show the effect of the *Lactobacillus brevis* G-101 on inhibition of inflammatory cytokine expression in LPS-stimulated peritoneal macrophages. FIG. 6a shows expression concentration of anti-inflammatory cytokine IL-10, FIG. 6b shows expression concentration of pro-inflammatory cytokine TNF-α, FIG. 6c shows expression concentration of IL-β, and FIG. 6d shows expression concentration of IL-6. (G3, $1 \times 10^3$ CFU; G4, $1 \times 10^4$ CFU; G5, $1 \times 10^5$ CFU)

Figure 7:
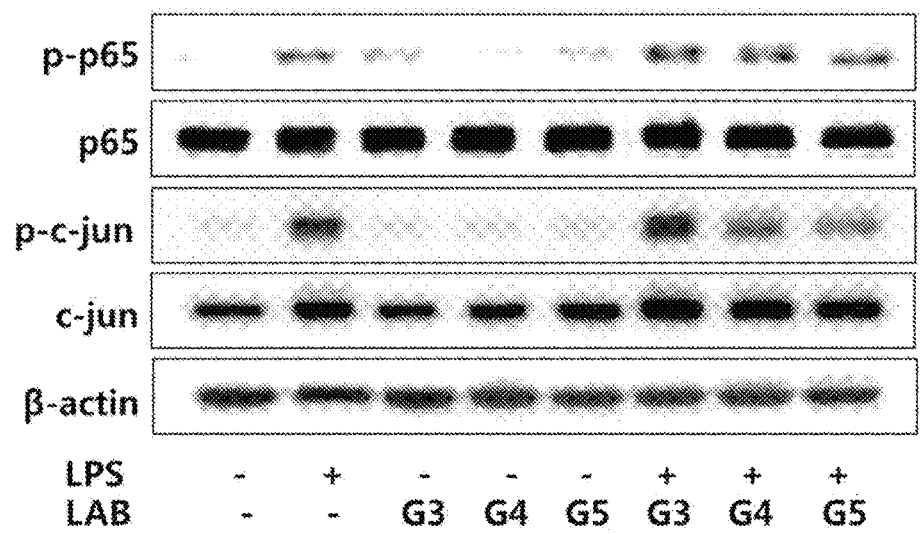

FIG. 7 shows effect of the *Lactobacillus brevis* G-101 on inhibiting of NF-B and AP1 activation in LPS-stimulated peritoneal macrophages. (G3, $1 \times 10^3$ CFU; G4, $1 \times 10^4$ CFU; G5, $1 \times 10^5$ CFU)

Figure 8:
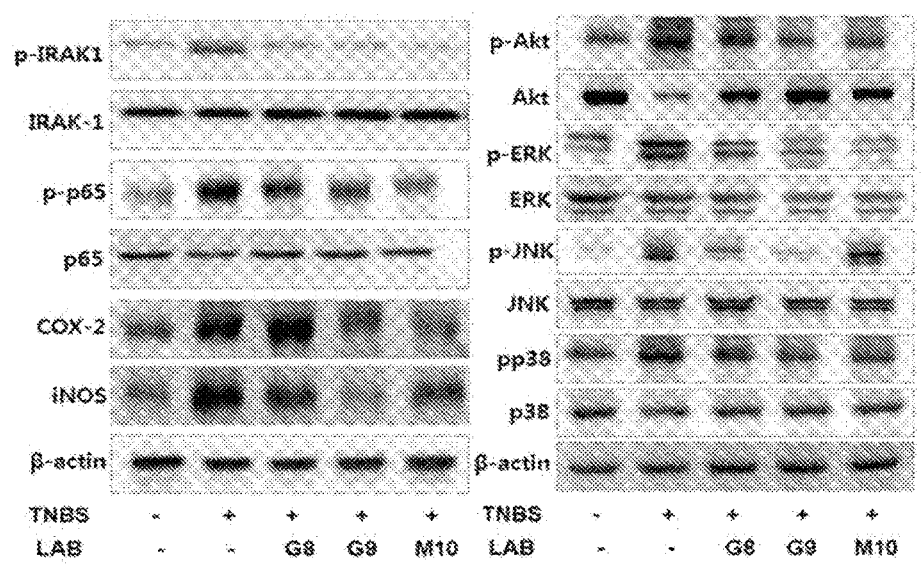

FIG. 8 shows inhibition effect of the *Lactobacillus brevis* G-101 affecting to NF-B, MAPKs and AKT signal pathway in TNBS-induced colitis mice. (G8, $1 \times 10^8$ *Lactobacillus brevis* G-101; G9, $1 \times 10^9$ *Lactobacillus brevis* G-101; M10, 10 mg/kg Mesalazine)

Figure 9:
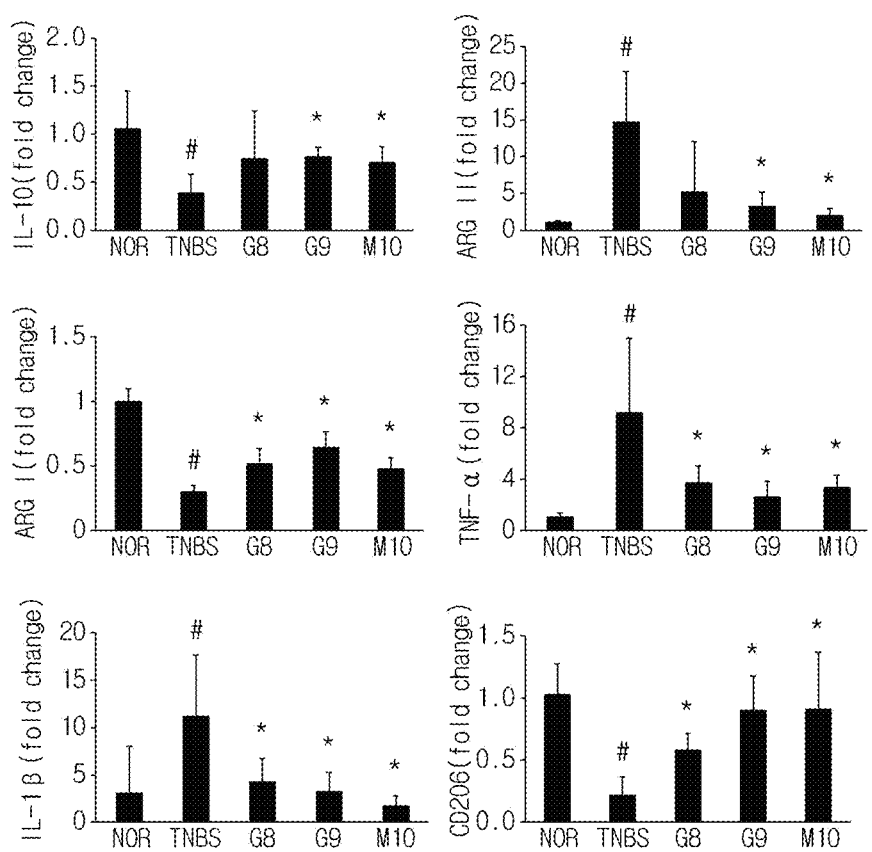

FIG. 9 shows inhibition effect of the *Lactobacillus brevis* G-101 affecting to macrophage polarization marker expression in TNBS-induced colitis mice. (G8, $1 \times 10^8$ *Lactobacillus brevis* G-101; G9, $1 \times 10^9$ *Lactobacillus brevis* G-101; M10, 10 mg/kg Mesalazine)

Figure 10A:
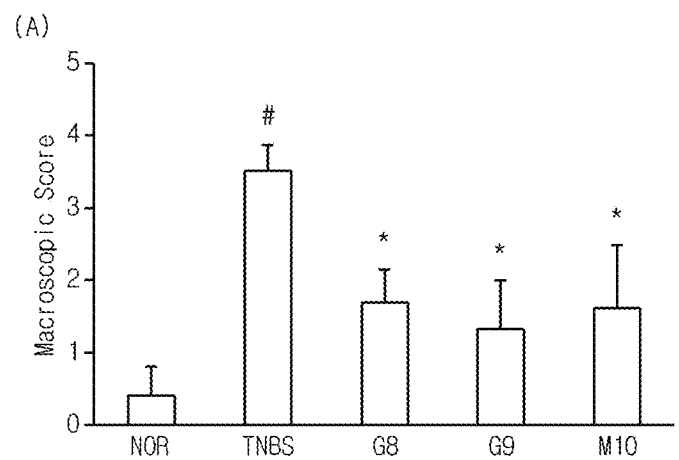
Figure 10B:
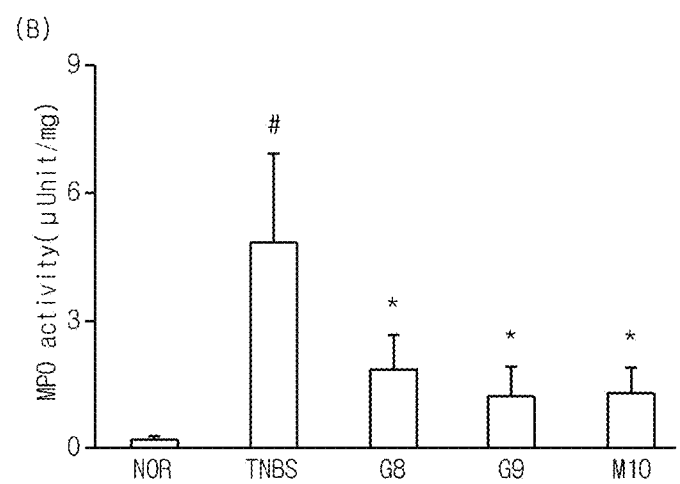
Figure 10C:
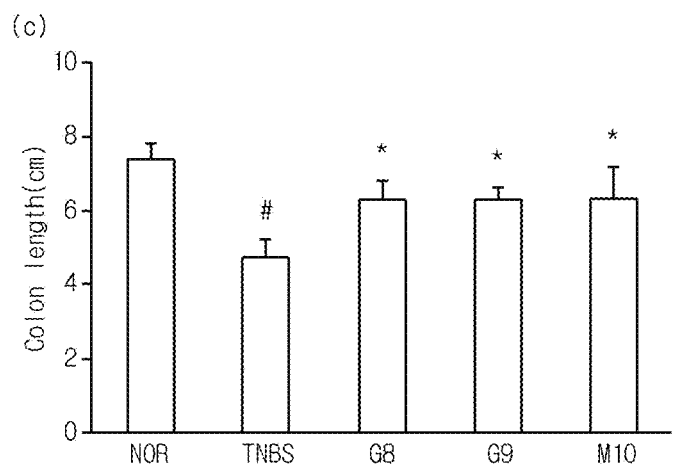
Figure 10D:
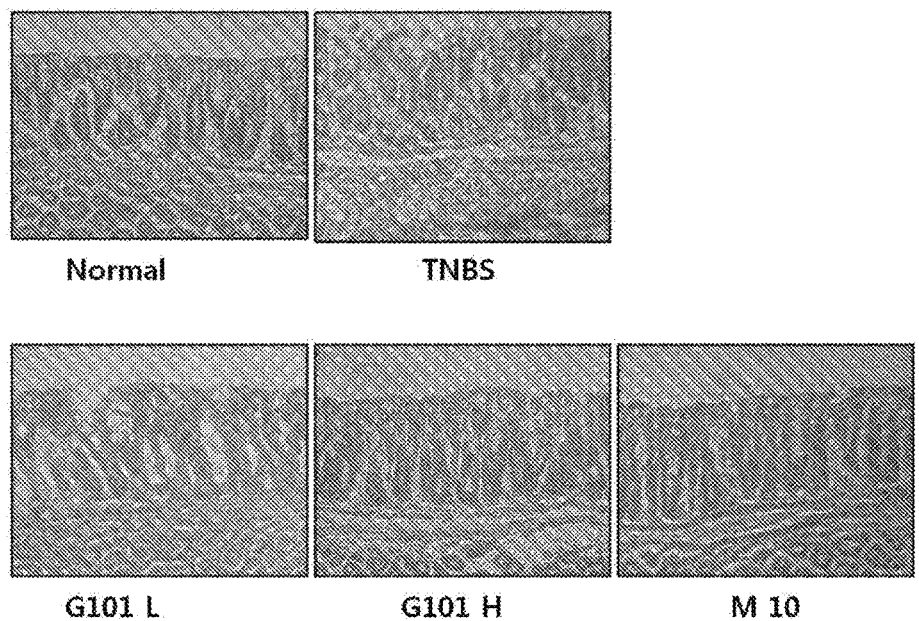

FIGS. 10a-10d show effect of the *Lactobacillus brevis* G-101 on macroscopic score (FIG. 10a) and colon length (FIG. 10b) of TNBS-induced colitis mice, inhibition effect thereof on myeloperoxidase activity (FIG. 10c) of TNBS-induced colitis mice, and the result of histological exam thereof (FIG. 10d). (G-8 or G101-L, $1 \times 10^8$ *Lactobacillus brevis* G-101; G-9 or G101-H, $1 \times 10^9$ *Lactobacillus brevis* G-101; M10, 10 mg/kg Mesalazine)

EMBODIMENTS

Hereinafter, embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just examples for the purpose of illustrations only, not intended to limit the scope of the disclosure, so it should be understood that other equivalents and modifications could be made thereto without departing from the scope of the disclosure.

EXAMPLES

Example 1. Isolation and Deposit of *Lactobacillus Brevis* G-101

A strain, which has high activity of decomposing MSG and converting thereof into GABA, was screened from *Lactobacillus* isolated form kimchi, and the strain showing the highest activity was selected, and then named G-101. As a result of 16S rRNA sequencing, the selected G-101 was confirmed to have homology of 97% or more with *Lactobacillus brevis*. Thus, it was identified as *L. brevis*.

Example 2. Effect of *Lactobacillus Brevis* G-101 on Inhibition of MSG Absorption (1) Experimental Method Male SD rats (200-220 g, 8 mice per group) were used as an experimental animal, MSG metabolic activity of intestinal microbiota in the experimental animal was checked before administrating the *Lactobacillus brevis* G-101. Then, the *Lactobacillus brevis* G-101 was administered into the experimental animal in an amount of $1 \times 10^9$ CFU/rat and $1 \times 10^{10}$ CFU/rat. Body weight, MSG concentration, microbial number grown in blood and digestive canal content (stomach, appendix), and harmful microbial enzyme activity in digestive canal were used as measurement index.

① Analysis of MSG Metabolic Activity of Intestinal Microbiota

In order to check MSG metabolic activity of intestinal microbiota in the experimental animal before administrating the *Lactobacillus brevis* G-101, intestinal content of the experimental animal administered with MSG was inoculated in MSG-containing MRS broth, cultured for 24 hours, and then MSG metabolic activity was measured by enzymatic analysis.

② MSG Administration

*Lactobacillus* was administered into the experimental animal for 3 days, MSG of 40 to 100 mg was orally administered thereinto, and after 15 min, 30 min, 60 min and 12 min, MSG concentration in digestive canal and blood was measured.

③ MSG Analysis

MSG was analyzed by using HPLC (Colum, Waters AccQ-tag column 3.9×150 mm; Eluent, acetate-phosphate buffer (AccQ-tag eluent A); Wavelength, Ex: 250 nm, Em 395 nm).

(2) Experimental Result: Effect of *Lactobacillus Brevis* G-101 on MSG Absorption As a result of analyzing MSG metabolic activity (specific activity) of the intestinal microbiota in the experimental animal by the enzymatic analysis, the activity was 0.0084 μmol/min/mg.

*Lactobacillus brevis* G-101 ($1 \times 10^9$ CFU or $1 \times 10^{10}$ CFU) was consecutively administered into a mouse for 3 days, and 30 min after the last administration, MSG of 1 g/kg was administered thereinto and then blood MSG was measured.

Figure 1:
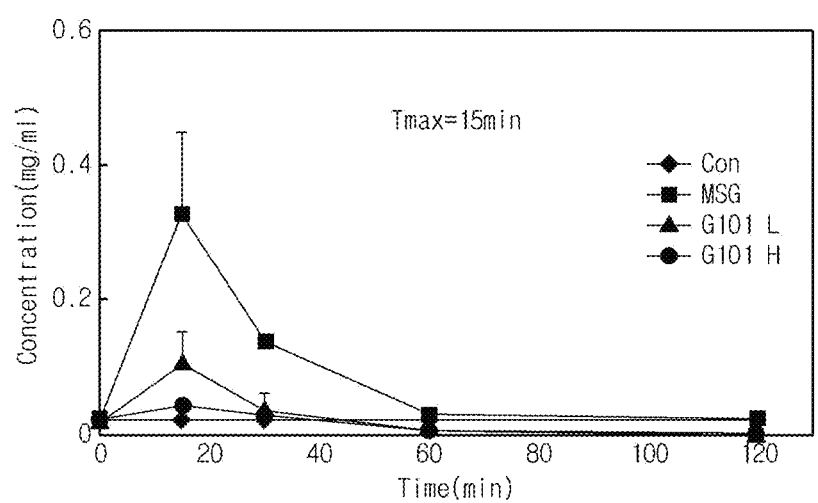
FIG. 1 shows blood MSG concentration over time after administering MSG into the rats administered with the *Lactobacillus brevis* G-101.

As a result, as shown in FIGS. 1 to 3, as compared to the group administered with only MSG, it was found that blood MSG concentration was significantly reduced by the administration of the *Lactobacillus brevis* G-101. Further, after taking MSG, Tmax, time to maximum blood MSG concentration, was not changed as 15 min, but in the case of administering the *Lactobacillus brevis* G-101 of $1 \times 10^{10}$ CFU, after taking MSG, in particular, reduction effect of Cmax, maximum blood MSG concentration, and AUC, total amount of MSG absorbed into blood, were excellent (FIG. 2).

Example 3. Effect of *Lactobacillus Brevis* G-101 on Conversion of MSG into GABA (1) Experimental Method As culturing *Lactobacillus* (*Lactobacillus brevis* G-101 and *Lactobacillus plantarum* CLP-0611 strain) together with MSG, conversion rate of MSG into GABA was measured. Two experiments were conducted: a method of inoculating the *Lactobacillus* (*Lactobacillus brevis* G-101 and *Lactobacillus plantarum* CLP-0611 strain) of 1% into MSG-containing MRS broth and then culturing thereof for 24 hours, and a method of inoculating the *Lactobacillus* (*Lactobacillus brevis* G-101 and *Lactobacillus plantarum* CLP-0611 strain) of 1% into MRS broth, culturing thereof for 24 hours, centrifuging thereof to collect cells and then adding the collected cells into MSG-added sterilized purified water to react thereof with the MSG. Whether the MSG was converted into GABA or not was analyzed by HPLC (Colum, Waters AccQ-tag column 3.9×150 mm; Eluent, acetate-phosphate buffer (AccQ-tag eluent A); Wavelength, Ex: 250 nm, Em 395 nm).

Further, MSG metabolic activity of the *Lactobacillus* (*Lactobacillus brevis* G-101 and *Lactobacillus plantarum* CLP-0611 strain) was analyzed by enzymatic analysis. Namely, the *Lactobacillus* (*Lactobacillus brevis* G-101 and *Lactobacillus plantarum* CLP-0611 strain) was inoculated into the MSG-containing MRS broth, cultured for 24 hours, and then the conversion rate of MSG was measured by the enzymatic analysis.

(2) Experimental Result: Result of Comparing MSG Decomposing Effect of *Lactobacillus Brevis* G-101 and *Lactobacillus Plantarum* CLP-0611

As culturing *Lactobacillus brevis* G-101 or *Lactobacillus plantarum* CLP-0611 strain together with MSG for 24 hours, conversion rate of MSG into GABA was measured by HPLC. As a result, as shown in FIG. 4a, FIG. 4b, FIG. 5a, and FIG. 5b, it was found that treatment with *Lactobacillus brevis* G-101 showed the best conversion rate, and about 2 to 5% of MSG was converted into GABA. In particular, in the case of inoculating the *Lactobacillus plantarum* CLP-0611 strain of 1% into the MSG-containing MRS broth followed by culturing thereof for 24 hours, the MSG was not converted into GABA. In addition, as a result of analyzing MSG metabolic activity by the enzymatic analysis, specific activity of the G-101 strain cultured in the MRS broth was 0.691 mmol/h/g, and that of the CLP0611 strain was 0.089 mmol/h/g.

Example 4. Effect of *Lactobacillus Brevis* G-101 on Inflammation Control by Macrophage Polarization (1) Experimental Method Male ICR mice (23-25 g, 8 mice per group) were used as an experimental animal, and *Lactobacillus brevis* G-101 was administered in an amount of $1\times10^9$ CFU/rat and $1\times10^{10}$ CFU/rat. Mesalazine was used as a control drug. Body weight, colon length, colonic myeloperoxidase, macroscopic score, colonic IL-β TNF-α, IL-6, NF-κβ, IKKβ, p-IKKβ, iNOS, COX-2β and HE exam were used as measurement index.

① TNBS-Induced Colitis Animal Model

The experimental animal was lightly anesthetized with ether, and a 1 ml round-tip syringe was inserted into the large intestine in depth of 3.5 to 4 cm through the anus. 100 µl of TNBS 2.5 mg/50% ethanol was slowly administered, and then the animal was kept vertically for 30 to 60 sec in order to make the material be spread well in the large intestine. Other experimental procedure was identical with the above colitis model experiment.

② Myeloperoxidase 0.5% hexa-decyl-trimethyl-ammonium bromide was added to intestinal mucous membrane tissue, and the tissue was homogenized followed by centrifuging at 8000 rpm for 30 min 1.6 mM tetra-methyl benzidine 100 µl, 0.1% $H_2O_2$ 5 µl, distilled water 795 µl were added to supernatant 100 µl, and then enzymatic activity change was measured in time course at 650 nm Enzymatic activity refers to an amount of an enzyme that oxidizes 1 µmol/ml of a substrate at 37° C. and is expressed as Unit/mg protein. Amount of protein was measured according to Bradford method.

③ Western Blot Analysis

Protein was obtained from intestinal mucous membrane by using lysis buffer. Loading buffer was added to the protein 50 µg followed by heating at 98° C. for protein denaturation. And, the protein was loaded on 10% SDS electrophoresis gel, and then transferred to a PVDF membrane at 30 V for 2 hours. It was blocked with 5% skim milk for about 2 hours, and then a primary antibody was bound thereto. It was washed with PBST, and then a secondary antibody was bound thereto. It was soaked in ECL solution to attach a fluorescent material, and then exposed to light and developed on a film.

(2) Experimental Result

① Effect of *Lactobacillus Brevis* G-101 on Anti-Inflammatory Cytokine Production in Macrophage In order to search *Lactobacillus* having anti-inflammatory effect from fermented food, *Lactobacillus*, which increases anti-inflammatory cytokine IL-10 production in LPS-induced peritoneal macrophage, was searched. As a result, the *Lactobacillus brevis* G-101 showed the strongest IL-10 production increasing effect, and when treated with the *Lactobacillus brevis* G-101 $1\times10^5$ CFU/ml, the production was recovered to 90% or more of normal cells. The *Lactobacillus brevis* G-101 inhibited inflammatory cytokines, TNF-α, IL-β and IL-6, in the LPS-stimulated peritoneal macrophage in a concentration-dependent manner (FIG. 6a to FIG. 6d). Further, the *Lactobacillus brevis* G-101 inhibited activation of inflammatory cytokine transcription factors, NF-κβ and AP1 (FIG. 7).

② Evaluation of Influence of *Lactobacillus Brevis* G-101 on Inflammatory Reaction Pathway In order to confirm the anti-inflammatory effect of the *Lactobacillus brevis* G-101, inflammation signal pathways of NF-B, MAPKs and AKT were measured. When treated with TNBS on a normal animal, it was observed that both of NF-κβ and MAPKs were activated, but activation was significantly inhibited in the group administered with the *Lactobacillus brevis* G-101. Further, the *Lactobacillus brevis* G-101 also inhibited IRAK1 phosphorylation reaction of the above inflammatory pathway. From this result, it was estimated that the *Lactobacillus brevis* G-101 regulates the upper pathway of the inflammatory reaction pathway (FIG. 8).

③ Effect of *Lactobacillus Brevis* G-101 on Macrophage Polarization Control

In the TNBS-induced colitis model animal, effect of controlling inflammatory cytokine expression and macrophage polarization was measured. Due to the TNBS treatment, inflammatory reaction-related M1 macrophage markers, ARGII, TNF-α and IL-1β were significantly increased, but those were inhibited by administration of the *Lactobacillus brevis* G-101. Further, M2 macrophage markers, ARG I, CD206 and IL-10 were inhibited by the TNBS, but those were increased by administration of the *Lactobacillus brevis* G-101 (FIG. 9).

④ Anti-Colitis Effect of *Lactobacillus Brevis* G-101

Anti-colitis effect of the *Lactobacillus brevis* G-101 was measured in the TNBS-induced colitis model animal. When treated with the TNBS on a normal animal with the TNBS, colitis index, macroscopic score, was increased (FIG. 10a), myeloperoxidase activity was increased (FIG. 10b), colon length was shortened (FIG. 10c), and tissue was changed (FIG. 10d). However, as a result of oral administration of the *Lactobacillus brevis* G-101, it could be observed that the colitis index was significantly inhibited.

Example 5. MSG Symptom Complex Attenuation Effect of *Lactobacillus Brevis* G-101

(1) Experimental Method 30 people experienced MSG Symptom Complex symptoms were selected, took the *Lactobacillus brevis* G-101 followed by eating MSG-added rice with Black Soybean Sauce, and then degree of MSG Symptom Complex symptoms was examined for about 12 days.

① Selection and Presentation of Sample

Both of a test group and a placebo food group were provided with a preparation in the form of 300 mg/capsule, and instructed to take 1 capsule/day. The test group took a capsule, which was manufactured to contain 10 billion of *Lactobacillus brevis* G-101 per capsule (300 mg) by mixing *Lactobacillus brevis* G-101 freeze-dried powder and maltodextrin, and the placebo food group took a capsule filled with 300 mg of maltodextrin per capsule.

For inducing MSG Symptom Complex, rice with black soybean sauce, in which the sauce contained 6 g of MSG in one portion, was prepared, and then provided to inspectors. The rice with black soybean sauce (one portion) was made of rice (180 g) and black soybean sauce (pork 40 g, Mirim ¼ Ts, onion 40 g, zucchini 40 g, carrot 30 g, cabbage 50 g, black soybean paste 1 Ts, cooking oil ½ Ts, seasoning (MSG, A company) 6 g, starch-water 2 Ts).

② Inspector

As an inspector, a panel was constituted with 30 selected people experienced MSG Symptom Complex symptoms, and any beverage or food other than water was not provided to the inspectors from 1 hour before evaluation.

③ Evaluation Content and Procedure

The inspectors were educated about characteristics of MSG Symptom Complex, divided into groups A and B, provided with G101 preparation or placebo food, and took thereof for 5 days. They were allowed to take the rice with black soybean sauce through total 2 visits. In order to ensure fairness for tasting, both preparations were provided as 300 mg/capsule not to let them know whether they took the G101 preparation or the placebo food, double blind placebo controlled study was conducted, and then the second test was conducted after the first test was completed.

In the first test (duration: 5 days), from Day 1 of research participation, the inspectors took the G101 preparation or the placebo food every day about at 10 a.m., and they visited at Day 5, took the rice with black soybean sauce about at noon, and then allowed to self-record about degree of MSG Symptom Complex symptoms (5 score scale: 1=No Symptom, 5=Strong Symptom), kinds and expression time of MSG Symptom Complex symptoms, and time spent on disappearance of the symptoms on questionnaire items.

Next week, the second test (Duration: 5 days) was identically conducted except for exchanging the G101 preparation or the placebo food between the groups A and B.

Namely, the first experiment and the second experiment were conducted as listed in the following Table.

TABLE 1

| Panel Collection | Group | Whether *Lactobacillus* preparation was provided or not | | | | |
|---|---|---|---|---|---|---|
| | | Mon | Tue | Wed | Thu | Fri |
| First Test | Group A | ○ | ○ | ○ | ○ | ○ |
| | Group B | X | X | X | X | X Take rice with black soybean sauce at noon |
| Second Test | Group A | X | X | X | X | X |
| | Group B | ○ | ○ | ○ | ○ | ○ Take rice with black soybean sauce at noon |

④ Statistical Treatment

Data was statistically treated using SAS Program 9.3. Significance of the data expressed as frequency and percentage was verified using $\chi^2$, and as the result of examining MSG Symptom Complex after eating the MSG-added rice with black soybean sauce by scoring the symptoms, preference was expressed as mean±standard deviation, difference between intake or non-intake of the *Lactobacillus* was verified using T-test.

(2) Experimental Result

① MSG Symptom Complex Symptoms after Eating Rice with Black Soybean Sauce 30 people experienced MSG Symptom Complex symptoms were selected out of people in their 20s to constitute a panel. The panel took the *Lactobacillus* preparation and the placebo preparation at the identical time in the morning for 5 days and the MSG-added rice with black soybean sauce, and then degree of MSG Symptom Complex symptoms was examined. As a result, as shown in Table 2, significance was shown depending on intake or non-intake of the *Lactobacillus* (p=0.0031).

In the G101 intake group, 'slight' subjective symptoms of MSG Symptom Complex was 33.3%, which was higher than 20% in the G101 non-intake group, and also in the G101 intake group, 'moderate' subjective symptoms of MSG Symptom Complex was 46.7%, which was higher than 16.7% in the G101 non-intake group. However, in the G101 non-intake group, 'slightly strong' subjective symptoms of MSG Symptom Complex was 43.3%, which was higher than 20.0% in the G101 intake group, and in the G101 non-intake group, 'strong' subjective symptoms of MSG Symptom Complex was 20%, but it was 0% in the G101 intake group.

Through this result, in both of the G101 intake group and the non-intake group, the subjective symptoms of MSG Symptom Complex after eating the MSG-added rice with black soybean sauce was shown, but it was found that the intake of the G101 can effectively inhibit the subjective symptoms of MSG Symptom Complex.

TABLE 2

| | *Lactobacillus Brevis* G101 | | |
|---|---|---|---|
| Symptom (Intensity) | Intake group N (%) | Non-intake group N (%) | |
| None | 0(0.0) | 0(0.0) | $\chi^2$ = 13.8421 |
| Slight | 10(33.3) | 6(20.0) | df = 4 |
| Moderate | 14(46.7) | 5(16.7) | p = 0.0031 |
| Slightly Strong | 6(20.0) | 13(43.3) | |
| Strong | 0(0.0) | 6(20.0) | |
| Total | 30(100.0) | 30(100.0) | |

Further, after eating the MSG-added rice with black soybean sauce, the symptoms of MSG Symptom Complex was scored (1=No Symptom, 5=Strong Symptom). As a result, as shown in Table 3, the subjective symptoms of MSG Symptom Complex in the G101 intake group (2.87) was significantly lower than that in the G101 non-intake group (3.63) (p=0.0016).

TABLE 3

| | *Lactobacillus Brevis* G101 | | |
|---|---|---|---|
| | Intake group | Non-intake group | T-value |
| Male (N = 10) + Female (N = 20) Total (N = 30) | 2.87 ± 0.73 | 3.63 ± 1.03 | −3.32 (p = 0.0016) |

The result of selecting all subjective symptoms of MSG Symptom Complex after eating the MSG-added rice with black soybean sauce was thirstiness (81.7%), drowsiness (66.7%), weakness (26.7%), tightness (11.7%), headache (10.0%), nausea (10.0%), dizziness (8.3%), indigestion (1.7%), palpitation (1.7%) and flushing (1.7%) in order, and there was no difference on the subjective symptoms according to whether the G101 was taken or not.

TABLE 4

| | *Lactobacillus Brevis* G101 | | | |
|---|---|---|---|---|
| Symptom | Intake group | Non-intake group | Total | |
| Thirstiness | 26(86.7) | 23(76.7) | 49(81.7) | $\chi^2$ = 3.5043(p = 0.3169) |
| Weakness | 6(20.0) | 10(33.3) | 16(26.7) | $\chi^2$ = 1.3636(p = 0.2429) |
| Palpitation | 0(0.0) | 1(3.3) | 1(1.7) | $\chi^2$ = 1.0169(p = 0.3132) |
| Tightness | 2(6.7) | 5(16.7) | 7(11.7) | $\chi^2$ = 1.4555(p = 0.2276) |

TABLE 4-continued

*Lactobacillus Brevis* G101

| Symptom | Intake group | Non-intake group | Total | |
|---|---|---|---|---|
| Flushing | 0(0.0) | 1(3.3) | 1(1.7) | $\chi^2 = 1.0169(p = 0.3132)$ |
| Dizziness | 1(3.3) | 4(13.3) | 5(8.3) | $\chi^2 = 1.9636(p = 0.1611)$ |
| Headache | 3(10.0) | 3(10.0) | 6(10.0) | $\chi^2 = 0.0000(p = 1.0000)$ |
| Nausea | 2(6.7) | 4(13.4) | 6(10.0) | $\chi^2 = 0.7407(p = 0.3894)$ |
| Drowsiness | 21(70.0) | 19(63.3) | 40(66.7) | $\chi^2 = 0.3000(p = 0.5839)$ |
| Indigestion | 0(0.0) | 1(3.3) | 1(1.7) | $\chi^2 = 1.0169(p = 0.3132)$ |
| Total | 30(100) | 30(100) | 60(100) | |

② MSG Symptom Complex Symptom Expression Time after Eating Rice with Black Soybean Sauce How long it will take to make the subjective symptoms of MSG Symptom Complex disappear was examined, and the result was shown in Table 5. As can be seen in Table 5, 96% or more of the subjective symptoms of MSG Symptom Complex disappeared within less than 4 hours in the G101 intake group, but 23.4% of the subjective symptoms of MSG Symptom Complex disappeared within less than 4 to 6 hours in the G101 non-intake group. Namely, in the G101 intake group, 69.9% of the MSG Symptom Complex symptoms disappeared within less than 3 hours, but only 39.0% of the MSG Symptom Complex symptoms disappeared in the G101 non-intake group within the same time period.

TABLE 5

*Lactobacillus Brevis* G101

| Time | Intake group N (%) | Non-intake group N (%) | |
|---|---|---|---|
| <1hr | 4(13.3) | 2(6.7) | $\chi^2 = 11.1404$ |
| 1 hr ≤ time < 2 hr | 10(33.3) | 5(16.5) | df = 6 |
| 2 hr ≤ time < 3 hr | 7(23.3) | 5(16.7) | p = 0.0841 |
| 3 hr ≤ time < 4 hr | 8(26.7) | 11(36.7) | |
| 4 hr ≤ time < 5 hr | 0(0.0) | 6(20.0) | |
| 5 hr ≤ time < 6 hr | 0(0.0) | 1(3.4) | |
| 6 hr ≤ | 1(3.4) | 0(0.0) | |
| Total | 30(100.0) | 30(100.0) | |

INDUSTRIAL APPLICABILITY

The *Lactobacillus brevis* G-101 according to the present invention showing anti-inflammatory activity is effective to improve, prevent, and treat inflammatory diseases, has excellent MSG decomposing ability, and in particular, exerts superior effect on inhibition of in vivo MSG absorption of an animal based on probiotic activity, which can maintain strain activity in a digestive canal, and excellent effect on attenuation of MSG Symptom Complex. Thus, it is expected to have various types of industrial applicabilities, for example, it can be used as a functional health food, a pharmaceutical composition, or a food product.

[Recognition of the Deposit of Microorganisms—Accession Number: KCCM11412P/Deposit Date: Apr. 30, 2013]

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To: CTCBIO Inc.
33 Hyundaikia-ro,
Paltan-myeon, Hwaseong-si,
Gyeonggi-do, 445-913, Korea RECEIPT IN THE CASE OF AN ORIGINAL issued pursuant to Rule 7.1 by the INTERNATIONAL DEPOSITARY AUTHORITY identified at the bottom of this page

| I. IDENTIFICATION OF THE MICROORGANISM | |
|---|---|
| Identification reference given by the DEPOSITOR: *Lactobacillus brevis* G101 | Accession number given by the INTERNATIONAL DEPOSITARY AUTHORITY: KCCM11412P |
| II. SCIENTIFIC DESCRIPTION AND/OR PROPOSED TAXONOMIC DESIGNATION | |
| The microorganism identified under I above was accompanied by:<br>☐ a scientific description<br>☐ a proposed taxonomic designation<br>(Mark with a cross where applicable) | |
| III. RECEIPT AND ACCEPTANCE | |
| This International Depositary Authority accepts the microorganism identified under I above, which was received by it on April 30, 2013. (date of the original deposit)[1] | |
| IV. INTERNATIONAL DEPOSITARY AUTHORITY | |
| Name: Korean Culture Center of Microorganisms<br>Address: 361-221, Yurim B/D<br>Hongje-1-dong<br>Seodaemun-gu<br>SEOUL 120-091<br>Republic of Korea | Signature(s) of person(s) having the power to represent the International Depositary Authority or of authorized official(s).<br>Date: April 30, 2013. |

[1] Where Rule 6.4(d) applies, such date is the date on which the status of international depositary authority was acquired; where a deposit made outside the Budapest Treaty after the acquisition of the status of international depositary authority is converted into a deposit under the Budapest Treaty, such date is the date on which the microorganism was received by the international depositary authority.

Form BP/4                                                                 Sole page The present disclosure has been described in detail. However, it should be understood that the detailed description and specific examples, while indicating embodiments of the disclosure, are given by way of illustration only, since various changes and modifications within the scope of the disclosure will become apparent to those skilled in the art from this detailed description.

What is claimed is:

1. A method of treating monosodium glutamate (MSG) symptom complex in a subject in need of such treatment, the method comprising:

orally administering an effective amount of live *Lactobacillus brevis* G-101 of (Accession Number: KCCM11412P) to the subject in need of such treatment.

2. The method of claim 1, wherein the effective amount is $1 \times 10^{10}$ CFU.

* * * * *